US012178812B2

United States Patent
Bhowmick et al.

(10) Patent No.: US 12,178,812 B2
(45) Date of Patent: *Dec. 31, 2024

(54) DOSAGE FORM OF VINCA ALKALOID DRUG

(71) Applicant: Sun Pharmaceutical Industries Limited, Mumbai (IN)

(72) Inventors: Subhas Balaram Bhowmick, Gujarat (IN); Prashant Kane, Gujarat (IN); Samarth Kumar, Gujarat (IN); Ramaji Karshanbhai Varu, Gujarat (IN); Nisarg Bipinchandra Mistry, Gujarat (IN); Swapnil Ramesh Patil, Gujarat (IN)

(73) Assignee: SUN PHARMACEUTICAL INDUSTRIES LIMITED, Mumbai (IN)

( * ) Notice: Subject to any disclaimer, the term of this patent is extended or adjusted under 35 U.S.C. 154(b) by 625 days.

This patent is subject to a terminal disclaimer.

(21) Appl. No.: 17/304,289

(22) Filed: Jun. 17, 2021

(65) Prior Publication Data

US 2021/0308118 A1    Oct. 7, 2021

Related U.S. Application Data

(63) Continuation of application No. 15/748,878, filed as application No. PCT/IN2016/050257 on Aug. 1, 2016, now Pat. No. 11,058,679.

(30) Foreign Application Priority Data

Aug. 1, 2015 (IN) .......................... 2910/MUM/2015

(51) Int. Cl.
| | |
|---|---|
| A61K 31/475 | (2006.01) |
| A61J 1/05 | (2006.01) |
| A61J 1/10 | (2006.01) |
| A61J 3/00 | (2006.01) |
| A61K 9/00 | (2006.01) |
| A61K 36/24 | (2006.01) |
| C07D 519/04 | (2006.01) |
| A61K 9/08 | (2006.01) |
| A61P 35/00 | (2006.01) |

(52) U.S. Cl.
CPC .............. *A61K 31/475* (2013.01); *A61J 1/05* (2013.01); *A61J 1/10* (2013.01); *A61J 3/002* (2013.01); *A61K 9/0019* (2013.01); *A61K 36/24* (2013.01); *C07D 519/04* (2013.01); *A61K 9/08* (2013.01); *A61P 35/00* (2018.01)

(58) Field of Classification Search
CPC .... A61K 31/475; A61K 9/0019; A61K 36/24; A61K 9/08; A61K 35/00; A61J 1/05; A61J 1/10; A61J 3/002; C07D 519/04
See application file for complete search history.

(56) References Cited

U.S. PATENT DOCUMENTS

| | | | |
|---|---|---|---|
| 4,150,744 | A | 4/1979 | Fennimore |
| 6,290,994 | B1 | 9/2001 | Lazaro Flores et al. |
| 11,058,679 | B2 | 7/2021 | Bhowmick et al. |
| 2007/0155768 | A1 | 7/2007 | Leverd et al. |
| 2008/0113042 | A1 | 5/2008 | Chu et al. |
| 2011/0295225 | A1 | 12/2011 | Wong et al. |
| 2015/0045289 | A1 | 2/2015 | West et al. |

FOREIGN PATENT DOCUMENTS

| | | |
|---|---|---|
| CN | 203208357 U | 9/2013 |
| EP | 0298192 A1 | 1/1989 |
| GB | 2125292 A | 3/1984 |

OTHER PUBLICATIONS

Beijnen J.H. ,Stability of intravenous admixtures of doxorubicin and vincristine, American Journal of Hospital Pharmacy, vol. 43,Nr 12; pp. 3022-3027.

Black J et al., Studies on the stability of Vinblastine sulfate in aqueous solution, Journal of Pharmaceutical Sciences, vol. 77,Nr 7, Jul. 1988; pp. 630-634.

Dine T et al., Stability and compatibility studies of vinblastine ,vincristine, ,vindesine and vinorelbine with PCV infusion bags, International Journal of Pharmaceutics, 77; 1991; pp. 279-285.

Extended European Search Report and Written Opinion for Application No. 16832433.3, issued by EPO on Feb. 26, 2019.

Indian Examination Report for Application No. 2910/MUM/2015, issued by the Intellectual Indian Property Office on Jan. 31, 2020.

International Search Report for PCT/IN2016/050257, mailed on Dec. 29, 2016.

Javlor Vinflunine Label; Summary of Product Characteristics; pp. 1-31.

Written Opinion of the International Searching Authority for PCT/IN2016/050257, completed on Dec. 13, 2016.

*Primary Examiner* — Zohreh A Fay
(74) *Attorney, Agent, or Firm* — Blank Rome LLP

(57) ABSTRACT

The present invention relates to a dosage form comprising an aqueous solution of a vinca alkaloid drug or its pharmaceutically acceptable salt in a flexible infusion container, and a light protective secondary packaging containing the flexible infusion container, wherein the dosage form is ready-to-infuse and wherein the aqueous solution is stable at room temperature.

10 Claims, No Drawings

DOSAGE FORM OF VINCA ALKALOID DRUG

This application is a continuation of U.S. patent application Ser. No. 15/748,878, filed Jan. 30, 2018, which is the U.S. national stage of International Patent Application No. PCT/IN2016/050257, filed Aug. 1, 2016, which claims the benefit of Indian Patent Application No. 2910/MUM/2015, filed Aug. 1, 2015, each of which is hereby incorporated by reference herein.

FIELD OF THE INVENTION

The present invention relates to a dosage form comprising a aqueous solution of a vinca alkaloid drug or its pharmaceutically acceptable salt in a flexible infusion container, wherein the dosage form is ready to infuse.

BACKGROUND OF THE INVENTION

Vinca alkaloid drugs, a class of anti-neoplastic agents, are derived from vinca alkaloids obtained from leaves of plant *Vinca rosea* or are of synthetic origin and are used for the treatment of various forms of cancers or tumors.

Available pharmaceutical formulations of the vinca alkaloid drugs are either lyophilized vials or concentrated solutions which require manipulation such as reconstitution and/or dilution prior to use. The labeling instructions of these products indicate that there is a high possibility of contact of these extremely potent oncolytic, cytostatic drugs, with hospital personnel and extreme care needs to be taken to avoid such instances. Further, improper reconstitution of the lyophilized formulations can create air-borne droplets hazardous to hospital personnel. There are chances of error in calculating the quantity of diluent and drug dosage which can result in accidental overdosages as the margin between toxic and therapeutic dosages are very small with the cytotoxic vinca alkaloid drugs. This can lead to fatal consequences. Because of their cytostatic nature, minimizing manipulation and contact of the drugs by hospital personnel and accurately calculating and administering dosages always remains a challenge. Further, the currently marketed products are available in glass vials or ampoules, which are difficult to handle and transport and are prone to breaking. Considering the drawbacks associated with conventional marketed products, the administration of these dosage forms entails proper handling and disposal. Clear instructions in this regard are therefore given in the package insert/label of the approved products. For instance label of approved product NAVELBINE®, a concentrated injection of vinorelbine tartrate to be diluted before administration, mentions following handling and disposal instructions—"Handle and dispose NAVELBINE consistent with recommendations for the handling and disposal of hazardous drugs. Exercise caution in handling and preparing the solution of NAVELBINE. The use of gloves is recommended. If the solution of NAVELBINE contacts the skin or mucosa, immediately wash the skin or mucosa thoroughly with soap and water. Avoid contamination of the eye with NAVELBINE. If exposure occurs, flush the eyes with water immediately and thoroughly".

Another problem associated with vinca alkaloid drugs is their sensitivity towards oxygen, air, and temperature, particularly in the presence of water, thus vinca alkaloid drugs in aqueous solutions, do not remain stable for prolonged period of time, since the active agent degrades quickly in aqueous solutions. The aqueous solutions of vinca alkaloid drugs are unstable when stored at room temperature. The label of currently marketed products entails storage of the drug solution at 2-8° C. such as in a refrigerator. For instance, Navelbine® label provides instructions to store the vials at 2-8° C. in a carton and further mentions that at 25° C., the unopened vials of Navelbine are stable only for 72 hours.

It is further noted that most of the reported dosage forms of vinca alkaloid drugs makes use of antioxidants to prevent oxidation and preservatives to maintain sterility. In case of solutions for parenteral administration, it is however desirable to keep the amount of excipients to a minimum, as these excipients can lead to undesirable interactions with the drug and may cause adverse effects.

Thus, there is a need for a dosage form of vinca alkaloid drugs which is ready to infuse and allows direct infusion of the drug solution in the desired dose to the patient without the need of any manipulation such as dilution or reconstitution before administration and moreover which also offers convenience in terms of handling, transportation and storage. Also, there is a need to provide a stable, solution of vinca alkaloid drugs which is stable at room temperature for a prolonged period of time, and which meets all acceptable stability criteria upon storage at room temperature for prolonged periods such as for at least 6 months, preferably 1 year or more. The present invention fulfills this need.

SUMMARY OF THE INVENTION

The present invention provides a dosage form comprising:
an aqueous solution comprising therapeutically effective amount of a vinca alkaloid drug or its pharmaceutically acceptable salt in a flexible infusion container and a light protective secondary packaging containing the flexible infusion container,
wherein the dosage form is ready-to-infuse and wherein the aqueous solution is stable at room temperature.

DETAILED DESCRIPTION OF THE INVENTION

The term "ready-to-infuse' is synonymous to the phrases 'directly administer' or 'directly administering' or 'direct intravenous infusion'. The term 'ready-to-infuse' as used herein means that the drug solution is sterile and suitable for direct intravenous infusion without manipulation, that is, no intermediate steps of dilution or reconstitution or dispensing or sterilization or transfer or handling and compounding are required before parenteral administration or infusion of the drug solution to the patient. Particularly, the volume of the aqueous solutions are large i.e more than 50 ml to as large as 3000 ml. The aqueous drug solution can be directly administered parenterally from the infusion container. The term "ready-to-infuse' also includes within its meaning administering the solution present in the infusion container without the need to monitor the volume infused. This eliminates the risk of any potential calculation or dilution error as well as risk of microbiological contamination prior to administration. This also eliminates or minimizes contact of the drugs by hospital personnel, thus avoiding any potential side effects associated with the cytotoxic anti-neoplastic drugs.

The term 'stable' at room temperature which means that the aqueous solution of the dosage form remains physically as well as chemically stable, when the dosage form is stored at room temperature (15° C.-35° C.) for at least six months, as demonstrated by compliance to acceptable specification/ limits, such as specified in United States Pharmacopoeia. The 'assay' of vinca alkaloid drugs remains within the specification range of 90% to 110% of label claim. Further, in accordance to the limits specified in United States Pharmacopoeia, the total impurities for vinorelbine remains not more than 2.0% by weight, and the total impurities for vincristine remains not more than 6.0% by weight, and the total impurities of vinblastine remains not more than 5% by weight upon storage of the dosage form at room temperature (15° C.-35° C.) for at least six months.

The term 'flexible' as used herein means that the infusion containers are made up of a material that provides flexibility to the container, and the container are not rigid such as containers made up of glass.

The term 'secondary packaging' as used herein means that the aqueous solution of a drug, in instant case, vinca alkaloids, is not in direct contact with the material of the secondary container such as an overwrap. The aqueous solution is in direct contact with the material of the primary container such as the flexible container, for example polymeric infusion bags in the instant invention and the secondary packaging comprise another container or pouch that overwraps or surrounds the inner flexible container.

The term 'about' as used herein within the specification before any value means, plus or minus 10% of the stated value.

The dosage form of the present invention comprises vinca alkaloid drugs or their pharmaceutically acceptable salts. The vinca alkaloid drugs are a class of anti-neoplastic agents, derived from vinca alkaloids of plants or of synthetic origin and are used in the treatment of various forms of cancers or tumors. The vinca alkaloid drugs that may be used according to the present invention include, but are not limited to, vincristine, vinblastine, vinorelbine, vindesine or their pharmaceutically acceptable salts. The dosage form of the present invention comprises a vinca alkaloid drug as the sole active agent. In one embodiment, the salt may be any suitable pharmaceutically acceptable salts, such as hydrochloride, sulfate, tartrate, bitartrate, citrate and the like. According to preferred embodiments, the vinca alkaloid drugs and pharmaceutically acceptable salt thereof include, but are not limited to, vincristine sulfate, vinblastine sulphate, vinorelbine tartrate, vindesine sulphate. The concentrations of the vinca alkaloids are expressed in mg/ml of the specific salt, however, the concentration range may vary depending upon the salt used in the dosage form of the present invention.

According to the present invention, the aqueous solution is free of preservatives, chelating agent, buffer or antioxidants. The dosage form of the present invention is designed for single use only and the remaining very small volumes, if any, should be discarded. In preferred embodiments, the dosage form of the present invention is also free of stabilizers such as anti-oxidants. It is surprisingly found that inspite of lack of an anti-oxidant, the dosage form is stable throughout the shelf life of the product, particularly it is stable at room temperature for at least 6 months, preferably one year or more.

The dosage form comprising an aqueous solution of vinca alkaloids has a pH in the range of about 3.0 to about 6.0, such as 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8 or 5.9, preferably from about pH 3.5 to about 5.0. The pH of the solution may be adjusted in the desired range by use of a suitable amount of pH adjusting agent known in the pharmaceutical art such as sodium hydroxide, hydrochloric acid, sulfuric acid or it may be auto-adjusted in the desired range by the ingredients present in the solution of the present invention. The aqueous solution according to the present invention is isosmotic or isotonic to the plasma fluids. The solution has an osmolality in the range of about 250-375 mOsm/kg, preferably 270-330 mOsm/kg such as 275, 280, 285, 290, 295, 300, 305, 310, 315, 320 or 325 mOsm/kg. The osmolality of the solution may be adjusted by addition of an osmotic agent or tonicity adjusting agent. The osmotic agent that may be used in the present invention may be selected from, but not limited to, dextrose, sodium chloride, potassium chloride, calcium chloride, mannitol, glycerol, sorbitol, propylene glycol, sucrose, and the like and mixtures thereof. The osmotic agent may be used in an amount suitable to maintain the osmolality of the solution in the range of about 250-375 mOsm/kg. According to one preferred embodiment, the osmotic agent is dextrose and it may be used in an amount ranging from about 1% w/v to about 5% w/v. According to other preferred embodiment, the osmotic agent is sodium chloride and it may be used in an amount ranging from about 0.3% w/v to about 1.0% w/v. In a preferred embodiment, the aqueous solution of vinca alkaloid drug according to the present invention has dissolved oxygen level of less than 4 ppm, such as less than 3, 2, 1, 0.5 or 0.1 ppm, preferably less than 2 ppm, more preferably less than 1 ppm. This is achieved by purging the aqueous solution with an inert gas such as nitrogen or argon or helium.

The dosage form of the present invention comprises a flexible infusion container. The flexible infusion container that may be used according to the present invention may be an infusion bag or a flexible pouch, soft bag or pouch, flexible infusion bottle, and the like. Particularly, the flexible infusion container is not impermeable in nature and possesses some permeation characteristics. The container is made up of a suitable material such as plastic or any other polymeric material. The container may include one or more layers of such materials. Such materials may be either polyolefins-polyethylene, polypropylene; polypropylene based polyolefin polymers; modified polyolefin-polyethylene polymers or styrene-polyolefin based polymers and block co-polymers thereof. These materials have some permeation properties and the aqueous solution of the vinca alkaloid drug is in contact with these materials of the container throughout the shelf life of the dosage form. The plastic material of the flexible container may be further coated or co-molded from outer side by one or more layers which may be made up of polyamide, modified polyolefin, polypropylene, styrene-polyolefin based polymers and block co-polymers thereof and the like. In one specific embodiment, the flexible infusion containers are made up of an outer layer of polyamide 11, a middle tie of modified polyolefin and an inner layer of linear low density polyethylene. This type of containers have a water vapour transmission rate of 2 g ($m^2$·day) when measured at (40° C./90% relative humidity); oxygen transmission rate of 900 ml/ ($m^2$·24 hour·atm) when measured at (23° C./0% relative humidity) and carbon dioxide transmission rate of 6000 ml/($m^2$·24 hour·atm) when measured at 23° C./0% relative humidity. Such containers are available commercially and are manufactured by Hosokawa. Alternatively, the flexible container may be a container marketed under the brand name of Technoflex which has an outer layer of polypropylene polymer with styrene-ethylene-butylene (SEB) block copolymer and the middle and inner layer of polypropylene based polyolefin polymer with styrene-ethylene butylene block copolymer. These types of containers have a water vapour transmission rate of 0.62 g ($m^2$·day) when measured at 23° C./60% relative humidity; oxygen permeability of 1110 ml/(m²·24 hour·atm) when measured at 23° C./40% relative humidity and carbon dioxide transmission rate of 5149 ml/(m²·24 hour·atm). In another embodiment, the flexible infusion container is made up of a material comprising a polymer of cyclic olefin such as cyclooolefin homopolymer or cycloolefin copolymer or mixture thereof. Specifically, in a particular embodiment, the flexible infusion container comprises an inner layer made up of a cycloolefin polymer, a middle layer made up of linear low density polyethylene polymer and an outer layer made up of low density polyethylene polymer. The inner layer remains in contact with the composition. Such containers are available commercially and are manufactured by Hosokawa as Polyelite EHC® film bag. These containers have a water vapour transmission rate of 2 g (m²·day) when measured at (40° C./90% relative humidity); oxygen transmission rate of 570 ml/(m²·24 hour·atm) when measured at (23° C./0% relative humidity) and carbon dioxide transmission rate of 3400 ml/(m²·24 hour·atm) when measured at 23° C./0% relative humidity. In another embodiment, the flexible container is made up of multilayer polyolefin film having layers from outside to inside made up of CPET-Tie-PE-Tie-EPC. Such containers are available as M312 and M312A® films by Sealer Air Corporation. These containers have a water vapour transmission rate of 5.0 g (m²·day) when measured at 38° C./100% relative humidity; oxygen transmission rate of 1315 cm³/(m²·24 hour·atm) when measured at 73° F./0% relative humidity and carbon dioxide transmission rate of 3945 cm³/(m²·24 hour·atm).

The infusion containers may include a Minitulipe® infusion port which is an infusion connector having three assembled parts including a central stopper made up of chlorobutyl rubber (latex free); an upper breakable part and a bottom part, both made up of polycarbonate. In one embodiment, the flexible infusion container contains a delivery port end for insertion of an infusion set cannula/needle. In one embodiment, the flexible infusion container/bag and the delivery port connecting to the infusion needle form a system whereby during administration of the solution to the patient the vacuum created by outgress of solution is accommodated by the elasticity or flexibility of the infusion bag instead of ingress of external non-sterile air. The dosage form can advantageously maintain the sterility of the solution until it reaches the patient.

The dosage form further comprises a light protective secondary packaging that surrounds the flexible infusion container. The light protective secondary packaging comprises a second container such as a pouch or overwrap, or film, made up of a suitable light protective material such as aluminum. Non limiting example of the material constituting secondary packaging or secondary containers include, aluminum, various polymers and copolymers like polyamide, ethylenevinyl alcohol copolymer etc. Aluminum based containers are preferred and include aluminium pouches, aluminium plated films, aluminium foils, aluminum laminate films, composite aluminum films co-extruded with other polymers like polyethylene, polypropylene, EVA, EMA, EAA etc. In one preferred embodiment, the secondary container is an overwrap pouch made up of composite polymer aluminium film having PET, Nylon-6, aluminium foil, and CPP (polypropylene/ethylene block copolymer) from outside to inside, the layers being either co-extruded and/or fixed using an adhesive with the other layer. In another preferred embodiment, the secondary container is an overwrap pouch made up of PET/NY/Aluminum/Oxygen absorbing layer/Polyethylene. In another preferred embodiment, the second container is an overwrap pouch made up of PET/NY/Aluminum/Oxygen absorbing layer/Polypropylene. In another preferred embodiment, the second container is an overwrap pouch made up of PET/NY/AL/OA/CPP. In some preferred embodiments, the dosage form may further comprise an oxygen scavenger, which may be placed in between the flexible infusion container and the second overwrap container or in some embodiments, the overwrap pouch may have a layer of oxygen absorbing material which acts as an oxygen scavenger, such as fused silica bags or iron containing adsorbents like iron oxide and the like. The oxygen scavenger or oxygen scavenging layer material may be a suitable material capable of quickly absorbing oxygen and having good oxygen absorbing capacity and heat resistance. Non-limiting example of such oxygen scavenging materials include iron, silica, charcoal etc. Preferably the oxygen scavenging material is iron based material. In one embodiment, the oxygen scavenger may be an iron based self-reacting type or iron based water dependent type oxygen scavenger/absorber (such as those marketed under the brand of AGELESS®). In one preferred embodiment, inert gas is present in the space between the flexible infusion container and light protective secondary packaging. The inert gas is used to flush out or replace the air between the space of the flexible infusion container and the light protective secondary packaging. The inert gas that may be used include, but is not limited to nitrogen, argon and helium. In one specific embodiment, the light protective secondary packaging comprises an aluminium pouch containing an oxygen scavenger and wherein the space between the flexible infusion container and light protective secondary packaging is occupied with an inert gas such as nitrogen.

According to one embodiment, the aqueous drug solution is filled in a flexible infusion container in such volumes, such that the solution occupies at least 90% of the volume and leaves a headspace less than 10%, such as less than 9, 8, 7, 6, 5, 4, 3, 2 or 1% of the volume of the container. Preferably, the headspace is less than 5% of the volume of the flexible infusion container, more preferably less than 2%. The flexible infusion container is filled with an aqueous solution of vinca alkaloid drug such that the head space volume is less than 5% of the volume of the flexible infusion container. A flexible infusion container used according to the present invention may be an infusion bag or a flexible pouch and the like.

In one embodiment, the vinca alkaloid drug is vinorelbine or a salt thereof, such as vinorelbine tartarate. It is present in the concentrations varying from about 0.01 mg/ml to 3.0 mg/ml, such as 0.02, 0.03, 0.04, 0.05, 0.06, 0.07, 0.08, 0.09, 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.4, 2.6, 2.6, 2.8 or 2.9 mg/ml preferably from 0.05 mg/ml to about 2.5 mg/ml, preferably 0.1 mg/ml to 1.0 mg/ml and wherein the volume of drug solution per unit dosage form may vary from about 20 ml to 1000, such as 25, 30, 35, 40, 50, 60, 70, 80, 90, 100, 110, 120, 130, 140, 150, 160, 170, 175, 180, 190, 200, 220, 240, 250, 260, 275, 300, 325, 350, 375, 400, 425, 450, 475, 500, 525, 550, 575, 600, 625, 650, 675, 700, 750, 800, 850, 900 or 950 ml, preferably from 25 ml to about 500 ml, more preferably from about 50 ml to 200 ml. In one preferred embodiment, the vinca alkaloid drug is vinorelbine tartrate and is present in the solution at a concentration range selected from, about 0.01 mg/ml to about 0.05 mg/ml, between 0.05 to 0.1 mg/ml, or from about 0.1 mg/ml to 1.0 mg/ml; wherein the volume of solution per unit infusion dosage form ranges from about 25 ml to 500 ml and wherein pH of the solution is in the range of about 3.5 to about 5.0. However, it is possible to use other concentration and volume of the aqueous solution depending upon the patient average body surface area of a patient, so that a single unit of the dosage form can cater the prescribed dose.

In one or more embodiments, the dosage form comprises an aqueous solution comprising vinorelbine or its pharmaceutically acceptable salt at a concentration of 0.01 mg/ml to 3.0 mg/ml and a pH of 3.5 to 5.0, in a flexible infusion container and a light protective secondary packaging containing the flexible infusion container, wherein the dosage form is ready-to-be infuse and wherein the aqueous solution is stable upon storage at room temperature for at least 6 months. The volume of solution per unit infusion dosage form may range from about 20 ml to 1000 ml. According to one particular embodiment, the dosage form comprises an aqueous solution comprising vinorelbine or its pharmaceutically acceptable salt at a concentration of 0.01 mg/ml to 3.0 mg/ml and a pH of 3.5 to 5.0, in a flexible infusion container and a light protective secondary packaging containing the flexible infusion container, wherein inert gas is present in the space between the flexible infusion container and the light protective secondary packaging. Such a dosage form is found to be stable upon storage at room temperature for at least 12 months. It is possible to incorporate an oxygen scavenger along with inert gas. The oxygen content of the aqueous solution may be controlled to less than 2 ppm. The flexible container is filled with the aqueous solution to at least 90% of the volume of the container, leaving a headspace of less than 10% of the volume of the container.

In one specific embodiment, the dosage form of the present invention comprises aqueous solution of vinorelbine tartrate, in a flexible infusion container. The flexible infusion container is made up of polyethylene which is the inner layer of the flexible infusion container and is in contact with the solution. The flexible container has towards the outer side, a middle tie made up of modified polyolefin and an outer layer of polyamide. These containers are have some degree of permeability to water vapor, oxygen and other gases. The light protective secondary packaging is made up of an aluminum pouch with an oxygen scavenger. Such a dosage form when subjected to stability studies at controlled room temperature (i.e. 25° C./40% relative humidity) as well as at 2-8° C., it was observed that after 12 months storage, the assay of vinorelbine remained within the specified limit of 90 to 110%, content of highest unknown impurity was within the specified limit of not more than 0.2% and content of total impurities was within the specified limit of not more than 2.0%. The content of related substances catharanthine, vinorelbine N-oxide, anhydrovinblastine N-oxide and anhydrovinblastine were within the specified limit of not more than 0.2%. The content of USP 3,6-epoxy vinorelbine was within the specified limit of not more than 1.0%. Further, the solutions were physically stable, with no precipitation or crystallization or color change observed upon storage.

The dosage form may be made available in different volumes and concentrations. For example vinorelbine or its salt like vinorelbine tartrate in aqueous solution at different concentrations and volumes, may be provided as below:

| S.No. | Vinorelbine Tartarate aqueous solution 0.6 mg/ml | | Vinorelbine Tartarate aqueous solution 0.05 mg/ml | | Vinorelbine Tartarate aqueous solution 0.025 mg/ml | |
|---|---|---|---|---|---|---|
| | Volume (ml) | Amount (mg) of drug in container | Volume (ml) | Amount (mg) of drug in container | Volume (ml) | Amount (mg) of drug in container |
| 1 | 50 | 30 | 40 | 2.0 | 20 | 0.5 |
| 2 | 80 | 48 | 50 | 2.5 | 25 | 0.625 |
| 3 | 100 | 60 | 60 | 3.0 | 30 | 0.75 |
| 4 | 110 | 66 | 70 | 3.5 | 40 | 1.0 |
| 5 | 125 | 75 | 80 | 4.0 | 50 | 1.25 |
| 6 | 150 | 90 | 90 | 4.5 | 60 | 1.5 |

In one embodiment, the vinca alkaloid drug is vincristine or a salt thereof, such as vincristine sulfate. It is present in the concentrations varying from about 0.0002 mg/ml to 0.2 mg/ml, such as 0.0003, 0.0004, 0.0005, 0.0006, 0.0007, 0.0008, 0.0009, 0.001, 0.002, 0.0025, 0.003, 0.0035, 0.004, 0.0045, 0.005, 0.0055, 0.006, 0.0075, 0.008 0.009, 0.010, 0.02, 0.03, 0.04, 0.05, 0.06, 0.07, 0.08, 0.09, 0.1, 0.11, 0.12, 0.13, 0.14, 0.15, 0.16, 0.17, 0.18 or 0.19 mg/ml, preferably from about 0.001 mg/ml to about 0.1 mg/ml mg/ml, and wherein the volume of drug solution per unit dosage form may range from about 10 ml to about 2000 ml, preferably from about 20 ml to about 1000 ml such as 25, 30, 35, 40, 50, 60, 70, 80, 90, 100, 110, 120, 130, 140, 150, 160, 170, 175, 180, 190, 200, 220, 240, 250, 260, 275, 300, 325, 350, 375, 400, 425, 450, 475, 500, 525, 550, 575, 600, 625, 650, 675, 700, 750, 800, 850, 900 or 950 ml, preferably from about 25 ml to 500 ml, more preferably from about 50 ml to 300 ml. In one preferred embodiment, vincristine sulfate is present in the solution at a concentration range selected from about 0.001 mg/ml to about 0.01 mg/ml, between 0.01 mg to 0.02 mg/ml or from about 0.02 mg/ml to 0.1 mg/ml, wherein the volume of solution per unit infusion dosage form ranges from about 25 ml to 300 ml and wherein pH of the solution is in the range of about 4.0 to about 6.0. However, it is possible to use other concentration and volume of the aqueous solution depending upon the patient average body surface area of a patient, so that a single unit of the dosage form can cater the prescribed dose.

According to one preferred embodiment, the dosage form comprises an aqueous solution comprising vincristine or its pharmaceutically acceptable salt at a concentration ranging from about 0.0002 mg/ml to about 0.1 mg/ml and a pH of 4.0 to 6.0, in a flexible infusion container and a light protective secondary packaging containing the flexible infusion container, wherein the space between the flexible infusion container and the light protective secondary packaging is occupied with an inert gas and an oxygen scavenger. The volume of solution per unit infusion dosage form may range from about 20 ml to 1000 ml. In such embodiments, the inner layer of the flexible infusion container is made up of polyethylene, that is the aqueous solution is directly in contact with polyethylene material. This inner layer is covered from outside by a middle tie made up of modified polyolefin and an outer layer of polyamide. These type of containers possess some degree of permeability to water vapor, oxygen and other gases. Preferably, in this embodiment, the solution have an oxygen content of less than 2 ppm and the solution occupies at least 90% of the volume of the container, leaving a headspace of less than 10% of the volume of the container. The dosage form when subjected to stability studies at controlled room temperature (i.e. 25° C./40% relative humidity) as well as at 2-8° C. for six months, it was observed the assay of vincristine upon storage remained within the specified limit of 90 to 110%, content of highest unknown impurity was within the specified limit of not more than 2.0%, the content of total impurities was within the specified limit of not more than 6.0%. Further, the content of related substances N-desformyl vincristine was within the specified limit of not more than 3.0%. Further, the solutions were physically stable, with no precipitation or crystallization or color change observed upon storage. It may be noted that the presence of an inert gas in between the light protective secondary packaging and the inner infusion container is important to achieve optimum room temperature stability to the dosage form. When an oxygen scavenger is included, the dosage form shows relatively improved stability profile, with lower levels of total impurities and N-desformyl vincristine.

The dosage form may be made available in different volumes and concentrations. For example vincristine or its salt like vincristine sulphate in aqueous solution at different concentrations and volumes, may be provided as below:

| S.No. | Vincristine aqueous solution 0.04 mg/ml | | Vincristine aqueous solution 0.015 mg/ml | | Vincristine aqueous solution 0.004 mg/ml | |
|---|---|---|---|---|---|---|
| | Volume (ml) | Amount (mg) of drug in container | Volume (ml) | Amount (mg) of drug in container | Volume (ml) | Amount (mg) of drug in container |
| 1 | 25 | 1.00 | 10 | 0.15 | 10 | 0.04 |
| 2 | 50 | 2.00 | 20 | 0.30 | 20 | 0.08 |
| 3 | 100 | 4.00 | 25 | 0.375 | 25 | 0.10 |
| 4 | 150 | 6.00 | 40 | 0.60 | 40 | 0.16 |
| 5 | 200 | 8.00 | 50 | 0.75 | 50 | 0.20 |
| 6 | 250 | 10.00 | 60 | 0.90 | 60 | 0.24 |

In one embodiment, the vinca alkaloid drug is vinblastine or a salt thereof, such as vinblastine sulfate, wherein the concentration of vinblastine sulfate in the aqueous solution may vary from about 0.001 mg/ml to about 3.0 mg/ml, such as 0.002, 0.003, 0.004, 0.005, 0.006, 0.007, 0.008, 0.009, 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.4, 2.6, 2.6, 2.8 or 2.9 preferably from about 0.01 mg/ml to about 2.0 mg/ml, and wherein the volume of drug solution per unit dosage form may range from about 10 ml to about 1000 ml, such as 20, 25, 30, 35, 40, 50, 60, 70, 80, 90, 100, 110, 120, 130, 140, 150, 160, 170, 175, 180, 190, 200, 220, 240, 250, 260, 275, 300, 325, 350, 375, 400, 425, 450, 475, 500, 525, 550, 575, 600, 625, 650, 675, 700, 750, 800, 850, 900 or 950 ml, preferably from 20 ml to 500 ml, more preferably from about 50 ml to 300 ml. In one preferred embodiment, vinblastine sulfate is present in the solution at a concentration range selected from about 0.001 mg/ml to about 0.01 mg/ml, between 0.01 mg to 0.075 mg/ml or from about 0.075 mg/ml to 0.2 mg/ml, wherein the volume of solution per unit infusion dosage form ranges from about 25 ml to 300 ml and wherein pH of the solution is in the range of about 3.5 to about 5.0. However, it is possible to use other concentration and volume of the aqueous solution depending upon the patient average body surface area of a patient, so that a single unit of the dosage form can cater the prescribed dose. In one or more embodiments, the dosage form comprises an aqueous solution comprising vinblastine or its pharmaceutically acceptable salt at a concentration of 0.001 mg/ml to 3.0 mg/ml and a pH of 3.5 to 5.0, in a flexible infusion container and a light protective secondary packaging containing the flexible infusion container, wherein the dosage form is ready-to-infuse and wherein the aqueous solution is stable upon storage at room temperature for 6 months.

According to one preferred embodiment, the dosage form comprises an aqueous solution comprising vinblastine or its pharmaceutically acceptable salt at a concentration of 0.001 mg/ml to 2.0 mg/ml and a pH of 3.5 to 5.0, in a flexible infusion container and a light protective secondary packaging containing the flexible infusion container, wherein inert gas and oxygen scavenger are present in the space between the flexible infusion container and the light protective secondary packaging such as aluminum pouch. The volume of solution per unit infusion dosage form may range from about 20 ml to 1000 ml. Optionally, the solution have an oxygen content of less than 2 ppm and the solution occupies at least 90% of the volume of the container, leaving a headspace of less than 10% of the volume of the container.

In certain embodiments of the dosage form of vinblastine sulphate, the inner layer of the flexible infusion container is made polyethylene that is the aqueous solution is in direct contact with the polyethylene material. This inner layer is covered from outside by a middle tie made up of modified polyolefin and an outer layer of polyamide. These containers are not impermeable, rather possess some degree of permeability to water vapor, oxygen and other gases. The dosage form when subjected to stability studies at controlled room temperature (i.e. 25° C./40% relative humidity) as well as at 2-8° C. for at least 6 months, provided assay of vinblastine which was within the specified limit of 90 to 110%, content of highest unknown impurity was within the specified limit of not more than 2.0% and content of total impurities was within the specified limit of not more than 5.0%. Further, the solutions were physically stable, with no precipitation or crystallization or color change observed upon storage.

The dosage form may be made available in different volumes and concentrations. For example vinblastine or its salt like vinblastine sulphate in aqueous solution at different concentrations and volumes, may be provided as below:

| S.No. | Vinblastine aqueous solution 0.1 mg/ml | | Vinblastine aqueous solution 0.01 mg/ml | | Vinblastine aqueous solution 0.005 mg/ml | |
|---|---|---|---|---|---|---|
| | Volume (ml) | Amount (mg) of drug in container | Volume (ml) | Amount (mg) of drug in container | Volume (ml) | Amount (mg) of drug in container |
| 1 | 50 | 5.0 | 20 | 0.2 | 20 | 0.10 |
| 2 | 100 | 10.0 | 25 | 0.25 | 25 | 0.125 |
| 3 | 150 | 15.0 | 30 | 0.3 | 30 | 0.15 |
| 4 | 200 | 20.0 | 35 | 0.35 | 35 | 0.175 |
| 5 | 250 | 25.0 | 40 | 0.4 | 40 | 0.20 |
| 6 | 300 | 30.0 | 45 | 0.45 | 45 | 0.225 |

The dosage form of the present invention is sterile and sterility of the aqueous solution is maintained throughout the shelf life period. The dosage form of the present invention may be sterilized by techniques such as membrane filtration (for example through a 0.22 micron membrane filter), radiation sterilization (for example gamma, electron beam, microwave) and/or ethylene oxide sterilization and the like. In one preferred embodiment, the ready to infuse dosage form of the present invention is sterilized by membrane filtration.

In preferred embodiments, the present invention provides a dosage form comprising an aqueous solution comprising therapeutically effective amount of a vinca alkaloid drug or its pharmaceutically acceptable salt in a flexible infusion container and a light protective secondary packaging containing the flexible infusion container, wherein the space between the flexible infusion container and the light protective secondary packaging is occupied with an inert gas, wherein the solution has a pH in the range of 3.0 to 6.0, wherein the vinca alkaloid drug or its pharmaceutically acceptable salt is selected from vinorelbine tartrate present at a concentration ranging from 0.01-3.0 mg/ml or vincristine sulphate present at a concentration ranging from 0.0002 to 0.2 mg/ml or vinblastine sulphate present at a concentration ranging from 0.001 to 3.0 mg/ml; wherein the dosage form is ready-to-infuse and wherein the aqueous solution is stable at room temperature. Preferably, according to this embodiment, the aqueous solution of vinca alkaloid drug has an oxygen content of less than 2 ppm and the secondary packaging has an oxygen scavenger and the volume of aqueous solution in the infusion container vary from 20 to 1000 ml.

The present invention provides a dosage form of vinca alkaloid drug as described herein for use as a medicament. The present invention provides a dosage form of vinca alkaloid drug as described herein for use in the treatment of neoplastic disease.

The dosage form of the present invention may be prepared by a process involving steps of—purging water for injection with Nitrogen gas to bring dissolved oxygen level below 2 PPM, preferably below 1 PPM. The Nitrogen gas was purged during the process to maintain dissolved oxygen level of less than 1 PPM. Adding and dissolving the osmotic agent such as dextrose or sodium chloride in the water for injection. Adding and dissolving the vinca alkaloid drug to the above solution. Checking and adjusting the pH of aqueous solution in the desired range of 3.0 to 6.0 using a suitable pH adjusting agent such as sodium hydroxide/hydrochloric acid/sulfuric acid. Adding sufficient quantity of water for injection to make up the final volume. Aseptically filtering the aqueous drug solution using a suitable membrane filter such as a 0.22 micron membrane filter. Filling the filtered aqueous solution into a flexible infusion container such as an infusion bag. Overwrapping the flexible infusion container by a light protective secondary packaging such as an aluminum pouch. Replacing the space between the infusion bag and the aluminum pouch with an inert gas such as nitrogen gas. Optionally, placing an oxygen scavenger in the space between the infusion bag and the aluminum pouch.

The present invention also provides in one embodiment, a process of filling the previously sterilized aqueous solution of the vinca alkaloid drugs into the flexible containers by especially designed closed systems that are interconnected to effect fluid transfer from one system to another while maintaining asepsis. The flexible containers are sterilized-in-place or sterilized while closed, prior to use. In specific embodiment, the components includes (a) a needle which penetrates the septum and opens/closes only after fully penetrating the septum to allow for fluid transfer into the flexible containers. The needle is usable for multiple penetrations; and (b) a septum which is highly deformable and expands before penetration to wipe the needle surface on both entry and removal. The septum is self-closing and is single use.

In the context of this specification "comprising" is to be interpreted as "including". Aspects of the invention comprising certain elements are also intended to extend to alternative embodiments "consisting" or "consisting essentially" of the relevant elements.

Where technically appropriate, embodiments of the invention may be combined.

Embodiments are described herein as comprising certain features/elements. The disclosure also extends to separate embodiments consisting or consisting essentially of said features/elements.

Any embodiments specifically and explicitly recited herein may form the basis of a disclaimer either alone or in combination with one or more further embodiments.

Hereinafter, the invention is more specifically described by way of examples. The examples are not intended to limit the scope of the invention and are merely used as illustrations.

EXAMPLE 1

According to preferred embodiments of the present invention, there is provided aqueous solution of vinorelbine tartrate and ready-to-infuse dosage form thereof.

TABLE 1

Details of the aqueous solution of vinorelbine tartrate

| Ingredients | Concentration mg/ml | |
| --- | --- | --- |
| | Example 1 (a) | Example 1 (b) |
| Vinorelbine tartrate eq. to vinorelbine base | 0.01-1.0 mg/ml | |
| Sodium Chloride | 0.9% | — |
| Dextrose | — | 5.0% |
| Sodium hydroxide/ Hydrochloric acid | q.s. to adjust the pH at 3.8-5.0 | q.s. to adjust the pH at 3.8-5.0 |
| Water for Injection | q.s. | q.s. |

Method of preparation: A portion of water for injection was collected in a beaker and purged with Nitrogen to bring the dissolved oxygen level to below 1 PPM. Dextrose/sodium chloride was added and dissolved in the water for injection. Nitrogen gas was further purged to maintain dissolved oxygen level of less than 1 PPM. The drug, vinorelbine tartrate was then added to the above solution and was dissolved by stirring. The pH of solution was checked and was adjusted to 4.5 using sodium hydroxide/hydrochloric acid. The volume was made up with water for injection along with stirring. The solution so prepared was filtered aseptically using a 0.2 micron membrane filter, followed by filling in a flexible container/infusion bag (marketed by Hosokawa). The filled infusion bags were sealed and were then overwrapped by a light protective secondary packaging, i.e. an aluminum pouch. An oxygen scavenger was placed in the space between the infusion bag and the aluminum pouch. The space between the infusion bag and the aluminum pouch was replaced with nitrogen gas.

The dosage form comprising aqueous solution of vinorelbine obtained according to the method above was subjected to stability studies at varying storage conditions (1) At controlled room temperature, i.e. 25° C./40% relative humidity (2) At 2-8° C. It was tested for the drug content (assay) and related substances, i.e. known and unknown impurities upon storage at different time points. It was found that all the stability criteria, such as assay of vinorelbine, content of related substances, and content of highest unknown impurity and total impurities were within the specified limits upon storage for 12 months. Further, the solutions were physically stable, with no precipitation or crystallization or color change observed upon storage. It was found that the assay of vinorelbine upon storage remained within the specified limit of 90 to 110%. The content of highest unknown impurity was within the specified limit of less than 0.2%. The content of total impurities was within the specified limit of not more than 2.0%. The content of related substances catharanthine, vinorelbine N-oxide, anhydrovinblastine N-oxide and anhydrovinblastine were within the specified limit of not more than 0.2%. The content of USP 3,6-epoxy vinorelbine was within the specified limit of not more than 1.0%.

In other experiments, wherein the solution of vinorelbine tartrate was filled in flexible infusion container, but was not overwrapped with the light protective secondary packaging and was exposed to light, it was found that the content of impurity 3,6 Epoxy vinorelbine when tested immediately after batch preparation was 0.7%, which upon stability went beyond the specified desired limit of not more than 1% within 1 month. Similarly the content of total impurities was 0.91% immediately after batch preparation, which upon stability went beyond the specified desired limit of not more than 2%.

The dosage form of the present invention includes various sizes of the flexible bags with varying volumes and having different concentrations, so that one container includes a specified amount of vinorelbine. These are presented below in Table 1a.

TABLE 1a

| S.No. | Vinorelbine Aqueous solution 0.6 mg/ml | | Vinorelbine Aqueous solution 0.05 mg/ml | | Vinorelbine Aqueous solution 0.025 mg/ml | |
|---|---|---|---|---|---|---|
| | Volume (ml) | Amount (mg) of drug in container | Volume (ml) | Amount (mg) of drug in container | Volume (ml) | Amount (mg) of drug in container |
| 1 | 50 | 30 | 40 | 2.0 | 20 | 0.5 |
| 2 | 80 | 48 | 50 | 2.5 | 25 | 0.625 |
| 3 | 100 | 60 | 60 | 3.0 | 30 | 0.75 |
| 4 | 110 | 66 | 70 | 3.5 | 40 | 1.0 |
| 5 | 125 | 75 | 80 | 4.0 | 50 | 1.25 |
| 6 | 150 | 90 | 90 | 4.5 | 60 | 1.5 |

EXAMPLE 2

According to one preferred embodiment of the present invention, this example provides an aqueous solution of vincristine sulfate and ready-to-infuse dosage form thereof:

TABLE 2

Details of the aqueous solution of Vincristine sulfate

| Ingredients | Concentration mg/ml |
|---|---|
| Vincristine sulfate | 0.001 mg/ml to 0.1 mg/ml |
| Dextrose, hydrous | 5.0% |
| Sodium hydroxide/sulphuric acid | q.s. to adjust the pH to 4.0-6.0 |
| Water for Injection | q.s. |

Method of preparation: A portion of water for injection was collected in a beaker and the purged with Nitrogen to bring the dissolved oxygen (level to below 1 PPM. Dextrose was added and dissolved in the water for injection. Nitrogen gas was further purged to maintain dissolved oxygen level of less than 1 PPM. The drug, vincristine sulfate was then added to the above solution and was dissolved by stirring. The pH of solution was checked and was adjusted to 4.5 using sodium hydroxide/sulfuric acid. The volume was made up with water for injection along with stirring. The Nitrogen gas purging was carried out continuously to maintain dissolved oxygen level <1 PPM. The solution so prepared was filtered aseptically using a 0.2 micron membrane filter, followed by filling in a flexible container like infusion bag (marketed by Hosokawa) and sealing of the containers. The filled infusion bags were overwrapped by a light protective secondary packaging, i.e. an aluminum pouch. An oxygen scavenger was placed in the space between the infusion bag and the aluminum pouch. The space between the infusion bag and the aluminum pouch was replaced with nitrogen gas.

The dosage form comprising aqueous solution of vincristine sulfate obtained according to the method above, was subjected to stability studies at varying storage conditions (1) At controlled room temperature, i.e. 25° C./40% Relative humidity (2) At 2-8° C. It was tested for the drug content (assay) and related substances, i.e. known and unknown impurities upon storage at different time points. It was found that various parameters after storage for six months, met all the stability criteria, such that the assay of vincristine, the content of related substances, and the content for highest unknown impurity and total impurities were within the specified limits. Further, the solutions were physically stable, with no precipitation or crystallization or color change observed upon storage. It was found that the assay of vincristine upon storage remained within the specified limit of 90 to 110%. The content of highest unknown impurity was within the specified limit of not more than 2.0%. The content of total impurities was within the specified limit of not more than 6.0%. The content of related substance N-desformyl vincristine was within the specified limit of not more than 3.0%.

In other experiments wherein the solution of vincristine sulphate was filled in flexible infusion container, but was not overwrapped with the light protective secondary packaging, it was found that the content of total impurities rose to unacceptably high levels of 8.8%; the level of N-desformyl vincristine impurity rose to unacceptably high levels of 7.16% and the assay of vincristine declined to 90%, when kept at room temperature for merely 10 days.

The dosage form of the present invention includes various sizes of the flexible bags with varying volumes and having different concentrations, so that one container includes a specified amount of vincristine. These are presented below in Table 2a.

TABLE 2a

| S.No. | Vincristine aqueous solution 0.04 mg/ml | | Vincristine aqueous solution 0.015 mg/ml | | Vincristine aqueous solution 0.004 mg/ml | |
|---|---|---|---|---|---|---|
| | Volume (ml) | Amount (mg) of drug in container | Volume (ml) | Amount (mg) of drug in container | Volume (ml) | Amount (mg) of drug in container |
| 1 | 25 | 1.00 | 10 | 0.15 | 10 | 0.04 |
| 2 | 50 | 2.00 | 20 | 0.30 | 20 | 0.08 |
| 3 | 100 | 4.00 | 25 | 0.375 | 25 | 0.10 |
| 4 | 150 | 6.00 | 40 | 0.60 | 40 | 0.16 |
| 5 | 200 | 8.00 | 50 | 0.75 | 50 | 0.20 |
| 6 | 250 | 10.00 | 60 | 0.90 | 60 | 0.24 |

EXAMPLE 3

According to one specific embodiment, this example provides an aqueous solution of vinblastine sulfate and its ready-to-infuse dosage form:

TABLE 3

Details of the aqueous solution of vinblastine sulfate

| Ingredients | Concentration mg/ml |
|---|---|
| Vinblastine sulfate | 0.001 mg/ml to 0.2 mg/ml |
| Sodium Chloride | 0.9% |
| Sodium hydroxide/Sulfuric acid | q.s. to adjust pH to 3.5-5.0 |
| Water for Injection | q.s. |

Method of preparation: A portion of water for injection was collected in a beaker and the purged with Nitrogen to bring the dissolved oxygen level to below 1 PPM. Sodium chloride was added and dissolved in the water for injection. Nitrogen gas was further purged to maintain dissolved oxygen level of less than 1 PPM. The drug, vinblastine sulfate was then added to the above solution and was dissolved by stirring. The pH of solution was checked and was adjusted to 4.25 using sodium hydroxide/sulfuric acid. The volume was made up with water for injection along with stirring. The Nitrogen gas purging was carried out continuously to maintain dissolved oxygen level <1 PPM. The solution so prepared was filtered aseptically using a 0.2 micron membrane filter, followed by filling in a flexible container like infusion bag (marketed by Hosokawa) and sealing of the containers. The filled infusion bags were overwrapped by a light protective secondary packaging i.e. an aluminum pouch. An oxygen scavenger was placed in the space between the infusion bag and the aluminum pouch. The space between the infusion bag and the aluminum pouch was replaced with nitrogen gas.

The dosage form comprising aqueous solution vinblastine sulphate was subjected to stability studies at varying storage conditions. (1) At controlled room temperature, i.e. 25° C./40% relative humidity (2) At 2-8° C. It was tested for the drug content (assay) and related substances, i.e. known and unknown impurities upon storage at different time points. It was found that all the stability criteria, such as assay of vinblastine, content of related substances, and content of highest unknown impurity and total impurities were within the specified limits, upon storage for 6 months. Further, the solutions were physically stable, with no precipitation or crystallization or color change observed upon storage. It was found that the assay of vinblastine upon storage remained within the specified limit of 90 to 110%. The content of highest unknown impurity was within the specified limit of not more than 2.0%. The content of total impurities was within the specified limit of not more than 5.0%.

In other experiments wherein the solution of vinblastine sulphate was filled in a flexible infusion container, but was not overwrapped with the light protective secondary packaging, then upon storage of the solution for merely 10 days, the level of total impurities increased significantly to 4.58% and the levels crossed the desired limit of not more than 5% when the solution was further kept at room temperature.

The dosage form of the present invention includes various sizes of the flexible bags with varying volumes and having different concentrations, so that one container includes a specified amount of vinblastine. These are presented below in Table 3a.

TABLE 3a

| | Vinblastine Aqueous solution 0.1 mg/ml | | Vinblastine Aqueous solution 0.01 mg/ml | | Vinblastine Aqueous solution 0.005 mg/ml | |
|---|---|---|---|---|---|---|
| S.No. | Volume (ml) | Amount (mg) of drug in container | Volume (ml) | Amount (mg) of drug in container | Volume (ml) | Amount (mg) of drug in container |
| 1 | 50 | 5.0 | 20 | 0.20 | 20 | 0.10 |
| 2 | 100 | 10.0 | 25 | 0.25 | 25 | 0.125 |
| 3 | 150 | 15.0 | 30 | 0.30 | 30 | 0.15 |
| 4 | 200 | 20.0 | 35 | 0.35 | 35 | 0.175 |
| 5 | 250 | 25.0 | 40 | 0.40 | 40 | 0.20 |
| 6 | 300 | 30.0 | 45 | 0.45 | 45 | 0.225 |

The invention claimed is:

1. A dosage form comprising:
   an aqueous solution comprising a therapeutically effective amount of a vinca alkaloid drug or its pharmaceutically acceptable salt in a flexible infusion container and a light protective secondary packaging containing the flexible infusion container, wherein
   (i) the vinca alkaloid drug is selected from the group consisting of vinorelbine, vincristine and vinblastine,
   (ii) the volume of solution per unit infusion dosage form ranges from about 20 ml to about 1000 ml,
   (iii) the dosage form is ready-to-infuse, and
   (iv) the aqueous solution is stable at room temperature.

2. The dosage form as claimed in claim 1, wherein the space between the flexible infusion container and the light protective secondary packaging is occupied with an inert gas.

3. The dosage form as claimed in claim 1, wherein the solution has an oxygen content of less than 2 ppm.

4. The dosage form as claimed in claim 1, wherein the solution has a pH in the range of 3.0 to 6.0.

5. The dosage form as claimed in claim 1, wherein the solution is free of preservative and anti-oxidant.

6. The dosage form as claimed in claim 1, wherein the solution occupies at least 90% of the volume of the container and leaves a headspace less than 10% of the volume of the container.

7. The dosage form as claimed in claim 1, wherein
   (i) the vinca alkaloid drug is vinorelbine tartrate and is present in the solution at a concentration range selected from about 0.01 mg/ml to about 0.05 mg/ml, about 0.05 to about 0.1 mg/ml, and about 0.1 mg/ml to about 1.0 mg/ml,
   (ii) the volume of solution per unit infusion dosage form ranges from about 25 ml to about 500 ml, and
   (iii) the pH of the solution is in the range of about 3.5 to about 5.0.

8. The dosage form as claimed in claim 1, wherein
   (i) the vinca alkaloid drug is vincristine sulfate, and is present in the solution at a concentration range selected from about 0.001 mg/ml to about 0.01 mg/ml, about 0.01 mg to about 0.02 mg/ml, or from about 0.02 mg/ml to about 0.1 mg/ml,
   (ii) the volume of solution per unit infusion dosage form ranges from about 25 ml to about 300 ml, and
   (iii) the pH of the solution is in the range of about 4.0 to about 6.0.

9. The dosage form as claimed in claim 1, wherein
   (i) the vinca alkaloid drug is vinblastine sulfate, and is present in the solution at a concentration range selected from about 0.001 mg/ml to about 0.01 mg/ml, about 0.01 mg to about 0.075 mg/ml, or from about 0.075 mg/ml to about 0.2 mg/ml,
(ii) the volume of solution per unit infusion dosage form ranges from about 25 ml to about 300 ml, and wherein
(iii) the pH of the solution is in the range of about 3.5 to about 5.0.

10. The dosage form as claimed in claim 1, wherein the volume of solution per unit infusion dosage form ranges from about 25 ml to about 300 ml.

* * * * *